US006921369B1

(12) United States Patent
Gehrke et al.

(10) Patent No.: US 6,921,369 B1
(45) Date of Patent: Jul. 26, 2005

(54) MOBILE ERGOSPIROMETRY SYSTEM (75) Inventors: Matthias Gehrke, Frankfurt/Main (DE); Ralf Henker, Leipzig (DE); Claus-Peter Kretschmer, Leipzip (DE); Thomas P. Kriesmer, Andernach (DE)

(73) Assignee: Cortex Biophysik GmbH, Leipzig (DE)

( * ) Notice: Subject to any disclaimer, the term of this patent is extended or adjusted under 35 U.S.C. 154(b) by 0 days.

(21) Appl. No.: 10/129,824

(22) PCT Filed: Sep. 21, 2000

(86) PCT No.: PCT/EP00/09259

§ 371 (c)(1),
(2), (4) Date: Aug. 16, 2002

(87) PCT Pub. No.: WO01/34022

PCT Pub. Date: May 17, 2001

(30) Foreign Application Priority Data

Nov. 9, 1999 (DE) .................................. 199 53 866

(51) Int. Cl.[7] .............................................. A61B 5/08
(52) U.S. Cl. ...................... 600/529; 600/301; 600/532; 600/538
(58) Field of Search ................................. 600/300–301, 600/529, 531–533, 538, 543; 455/62; 73/23.3; 704/258; 340/384.1

(56) References Cited

U.S. PATENT DOCUMENTS

| 3,694,811 | A | * | 9/1972 | Wood ....................... 340/825.2 |
| 4,155,040 | A | * | 5/1979 | Harmon et al. ............... 455/88 |
| 4,658,832 | A | * | 4/1987 | Brugnoli ..................... 600/532 |
| 4,862,514 | A | * | 8/1989 | Kedjierski ................ 455/161.2 |
| 5,510,269 | A | * | 4/1996 | Black et al. ................. 436/164 |
| 5,544,649 | A | * | 8/1996 | David et al. ................. 600/301 |
| 5,754,944 | A | * | 5/1998 | Dominiak et al. .......... 340/7.42 |
| 5,857,939 | A | * | 1/1999 | Kaufman ........................ 482/8 |
| 6,126,613 | A | * | 10/2000 | Edwards et al. ............. 600/539 |

(Continued)

FOREIGN PATENT DOCUMENTS

EP 0 846 440 6/1998

(Continued)

*Primary Examiner*—Robert L Nasser
*Assistant Examiner*—Patricia Mallari
(74) *Attorney, Agent, or Firm*—Oblon, Spivak, McClelland, Maier & Neustadt, P.C.

(57) ABSTRACT

A mobile ergospirometry system including a portable measurement unit that can be attached to a subject and that incorporates a mouthpiece or mask to collect respiratory gas, a sensor for the volume or amount of gas as well as sensors to determine the $CO_2/O_2$ concentration in the respiratory gas, a signal processing unit, and a telemetry module. The system further includes a computer-assisted base station having a telemetry unit to create a wireless connection to the telemetry module. In the system a bidirectional transmission route to the telemetry unit is set up by the telemetry module to transmit data and commands, for which purpose a transmitter and receiver subassembly is provided in each case, so that from the base station it is possible to communicate to the subject online information or requirements for operation of the measurement unit and/or the progress of the test. The signal processing unit sends coded commands that it receives to a speech module for the conversion and audio output of instructions as to behavior, explanations, or similar information.

15 Claims, 4 Drawing Sheets

U.S. PATENT DOCUMENTS 6,162,180 A * 12/2000 Miesel et al. ............... 600/481
6,398,727 B1 * 6/2002 Bui et al. .................... 600/300
6,443,890 B1 * 9/2002 Schulze et al. ............. 600/300
6,493,546 B2 * 12/2002 Patsiokas ................. 455/277.1

FOREIGN PATENT DOCUMENTS

WO          98 53732          12/1998
WO      WO 98/53732      * 12/1998   ............ A61B 5/00

* cited by examiner

MOBILE ERGOSPIROMETRY SYSTEM

DESCRIPTION

The invention relates to a mobile ergospirometry system according to the precharacterizing clause of claim 1. That is, it comprises firstly a portable measurement unit that can be attached to the subject and incorporates a mouthpiece or mask to collect respiratory gas, a sensor for the volume or amount of gas as well as sensors to determine the $CO_2/O_2$ concentration in the respiratory gas, a signal-processing system and a telemetry module. Secondly, it comprises a computer-assisted base station having a telemetry unit to create a wireless connection with the telemetry module of the portable unit.

Mobile ergospirometry devices, e.g. for stress studies outside the laboratory, have been known for some years. With such mobile systems analyses can be carried out directly on the sports field or in the workplace, under natural conditions and in stress situations. Telemetry units are used to transmit the measured data in real time to a personal computer or a notebook, so that after evaluation of the data the training or practice session can be appropriately controlled. Such devices have opened up new applications in the medical diagnosis of performance, in the areas of work, sport and rehabilitation medicine.

The patent PCT-WO 98/53732 discloses a portable ergospirometry system with a telemetric data-transfer unit. With the arrangement described there, individual parameters of oxygen uptake and carbon dioxide production can be monitored, enabling a respiratory analysis to be combined with the measurement of the cardiac rhythm under natural ambient conditions.

According to this known teaching, a portable unit attached to a subject comprises, in addition to a breathing mask, a gas-analysis device to determine the $O_2$ and $CO_2$ values of the gas to be meaured. In addition a heart-rate monitor is provided, the output signals of which are transmitted to a microprocessor that is a component of the portable unit. The measured values are deposited in an internal memory and by way of a telemetry component are transferred to a telemetry receiver, which in turn is connected to a personal computer system.

The volume flow of the respiratory gas is measured, according to the patent PCT-WO 98/53732, by a special flowmeter comprising rotating vanes, the movement of which is monitored by an infrared light-emitting diode element.

The telemetric data-transmission route between the portable unit and the base station plus personal computer allows the data measured by the ergospirometer to be assembled for display and subsequent evaluation and processing.

However, additional measures beyond those provided in the state of the art would be required to allow a doctor in charge to take an active part in determining the details of the test, so as to make the values obtained more useful for diagnosis.

Furthermore, the known portable system is elaborate and complicated to use, and too much time is required to instruct frequently changing subjects.

Hence it is the objective of the invention to provide a further developed mobile ergospirometry system comprising a portable measurement unit that can be attached to a subject as well as a computer assisted base station, such that with this system it is possible to influence and optimize the course of the test by direct online input, while simultaneously such systems will be more readily accepted by both subjects and the person responsible for carrying out the test. In addition, it is intended to provide an opportunity to store the measured data in the portable measurement unit in such a way as to optimize the memory space, so that even if the telemetric means of data transmission should undergo temporary failure, the data will be preserved, so that in turn the number of experiments and hence the stress on the subject can be minimized.

The objective of the invention is achieved by a mobile ergospirometry system according to the characteristics given in claim 1, whereas the subordinate claims comprise at least advantageous embodiments and further developments.

Accordingly, the basic idea of the invention consists in disclosing a special bidirectional telemetry element with a speech module to assist its operation, so that information or instructions regarding operation of the measurement unit and/or the progress of the test can be communicated by the person in charge of conducting the test, i.e. transmitted to the subject. It is also possible for technical information regarding the apparatus to be output by acoustic means; for instance, a subject testing himself can report, e.g., "defect in respiratory-gas tube".

In accordance with the invention the signal processor of the portable measurement unit is capable of conducting coded commands that it receives to a speech module for conversion, the latter being so designed that it can emit audio signals representing instructions as to the subject's behavior or other instructions as well as information about the measured data. These signals can then be made available to the subject by way, for instance, of an earphone or another auditory transducer.

The portable measurement unit is designed so that it fulfills all the functions of an ergospirometry system, including calculation and storage of measured values as well as control of the operating, measurement and communication functions. In a preferred embodiment of the invention the telemetry unit in the ase station comprises an automatic frequency selection device, so that after scanning of the frequency band and/or after a procedure for transmission of test data and evaluation of the result of that transmission, it is possible to determine the telemetry frequency at which the transmission quality can be expected to be optimal. This test transmission can be carried out at the beginning of the experiment, in which case it is also conceivable for the check to be repeated automatically on the basis of, e.g., monitoring the field strength of the signals being received.

In addition to the heart-rate detector integrated into the measurement unit, a multi-channel ECG module is provided, such that the ergospirometric and the cardiological data are monitored synchronously with reference to the signal processor. As a result of this synchronized collection and presentation of the measured data, the temporal relation between the values is immediately discernible, which increases the diagnostic relevance and information content of the data.

For intermediate storage, in particular for the purpose of backing up the data, in the measurement unit a memory is provided, so designed that data sets can be deposited in a selectable format, with reference either to each breath that is drawn or to a prespecified period or interval of time. The signal processor enables the ergospirometry values to be calculated from the collected data, the results of the calculations being stored in memory and/or displayed or communicated to the subject.

The signal processor is able to detect behavioral instructions on the basis of an external command or automatically, taking into account the sequence of events actually occurring or data actually being collected in comparison to the planned course of the test, and to communicate these to the subject by way of the speech module. For this purpose, the speech module contains a digital memory in which are deposited words, word groups and other items of information that can be audibly represented.

By means of the signal processor, from the words or groups of words stored in the digital memory it is possible to select, combine and transmit in a controlled manner a set of words representing the current command.

By way of additional sensors in the portable measurement unit, the values signalled by the respiratory-gas sensors can be calibrated and corrected, e.g. by measuring the ambient temperature or the humidity of the respiratory gas.

The portable measurement unit offers not only a means of telemetric data transmission but also a standard interface for the transmission, preferably by wire, of data to the base station or to a personal computer equipped with the appropriate evaluation software.

The base station comprises an interface to produce a connection to a bidirectional telemetry unit, which can be designed as a supplementary subassembly. Thus, for instance, the base station can be set up in the form of a personal computer at the workplace of the person conducting the test, whereas the telemetry unit is separately positioned at a site that is optimal for high-frequency transmission.

Functionally, the portable measurement unit is organized in such a way that all the hardware components are subdivided between two housings of nearly equal weight and size. The two housings are connected to one another by a cable. A carrier system is provided so that the bipartite measurement unit can be supported in the shoulder/clavicular region of the subject, so that the subject can move almost without restriction and does not experience the measurement unit as an extra load. Because the attachment point is in the very upper part of the body, conduits from the mouthpiece or the mask can be made quite short, and the antenna to radiate signals from the telemetry module functions optimally.

It is also preferred to integrate into one of the housings secondary elements to serve as a power supply. This eliminates the need for the subject to carry a separate element with storage batteries and associated cables to connect them to the actual measurement unit.

In at least one of the housings operating and display means are present, e.g. in the form of membrane keys combined with light-emitting diodes, which enable the subject to communicate audiovisually with the measurement unit and to operate the unit.

The signal preprocessing with respect to calculation of the ergospirometry parameters in the portable measurement unit itself is designed so that the subject can receive information directly from the measurement unit. Hence the portable measurement unit can also be operated independently, in which case the measured data are stored in the above-mentioned memory. It is then easily possible to evaluate the data at a later time, by simply downloading them.

The memory for data backup in the portable measurement unit is designed such that the memory contents are preserved for a specified time even after the unit has been turned off. By means of the signal-processing system the portable memory unit is able to convert entirely to internal storage when an interruption in the telemetric data transfer is detected, with no need to repeat the ergospirometrically relevant exercise: the measured data are basically buffered in intermediate storage.

In one embodiment of the invention the measurement unit can comprise additional interfaces for the connection of supplementary devices or sensors, by means of which, for example, vital body functions can be assessed by measuring blood pressure, skin temperature or the like, and hence can be taken into account as the test proceeds.

The "intelligent" software underlying vocal control of the portable measurement unit enables digitally stored and/or synthetically generated words or word groups to be emitted directly, but also to be linked together with reference to particular requirements or commands. These commands can be initiated by the person conducting the experiment or test, by way of the telemetry module in the base station, but can also be generated automatically by the measurement unit itself, whenever certain measurement or control values are encountered during a test.

In the following the invention is explained with reference to an exemplary embodiment with the aid of drawings, wherein.

Figure 1:
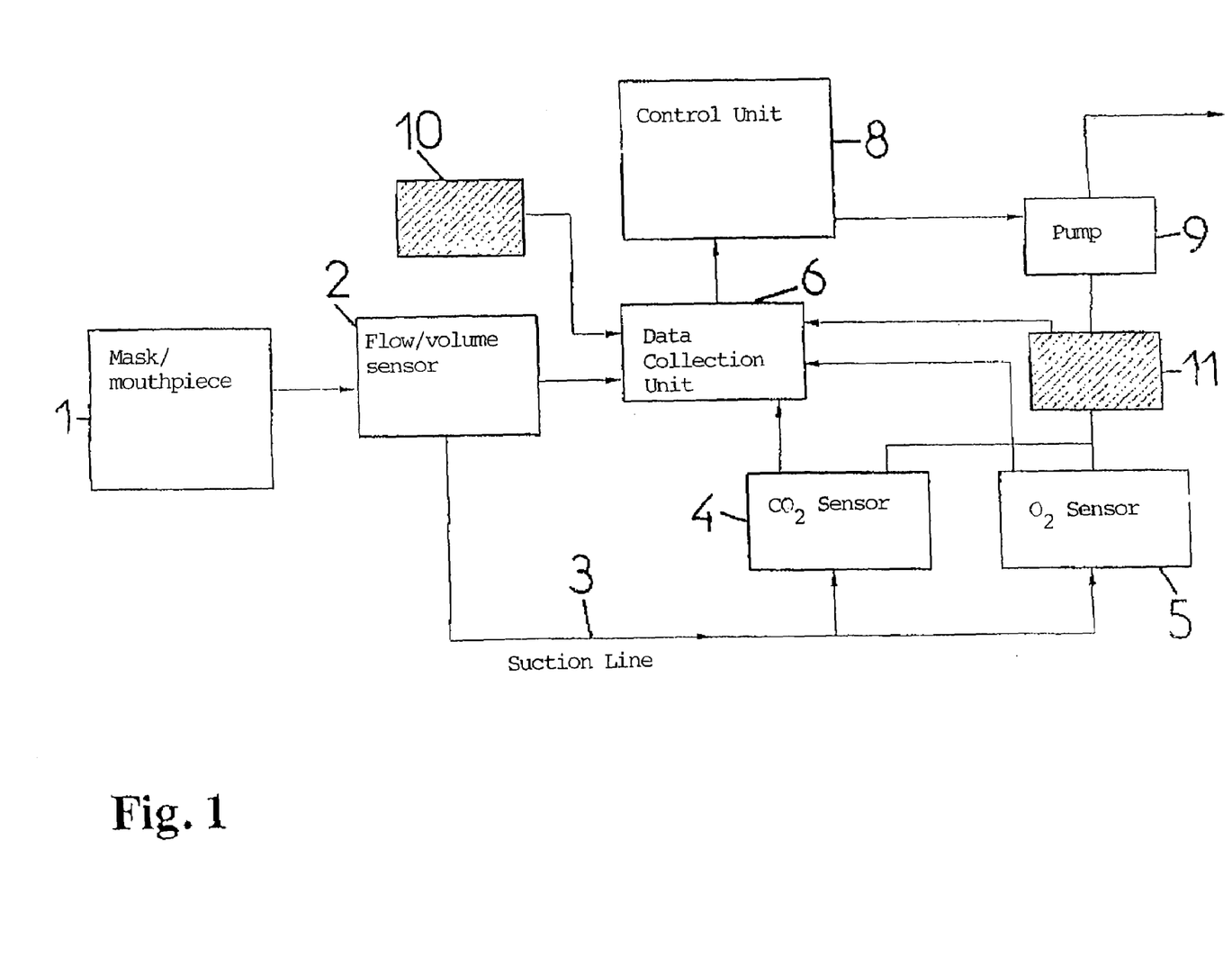
FIG. 1 shows typical functional units of an ergospirometry system.

An ergospirometry system such as is shown in FIG. 1 has as its input a face mask or a mouthpiece 1, which sends respiratory gas through a flow/volume sensor 2; a suction line 3 then conducts the gas to sensors 4 and 5, which determine its $CO_2$ and $O_2$ concentration, respectively.

When the respiratory gas is guided in such a way, measured values can in principle be obtained in a breath-by-breath procedure, but a gas-mixing chamber can also be used. In order to achieve the desired optimization of an ergospirometric analysis with correspondingly high signal resolution, preference is given to the breath-by-breath procedure.

The output data from the flow or volume sensor 2 and the $CO_2/O_2$ sensors 4, 5 are sent to a data-collection unit 6, which is connected to a processor 8 for controlling the sequence of measurements as well as evaluating the measurement signals. The control unit 8 is likewise capable of sending signals to a gas pump 9, so that the desired flow levels in the suction line 3 are maintained or achieved.

In addition, it is possible for the data-collection unit 6 to receive signals from other sensors, e.g. a sensor 10 for the ambient temperature and/or a sensor 11 for humidity. These last sensor signals can be used to calibrate or correct the respiratory-gas analysis derived from the sensors 4 and 5.

Figure 2:
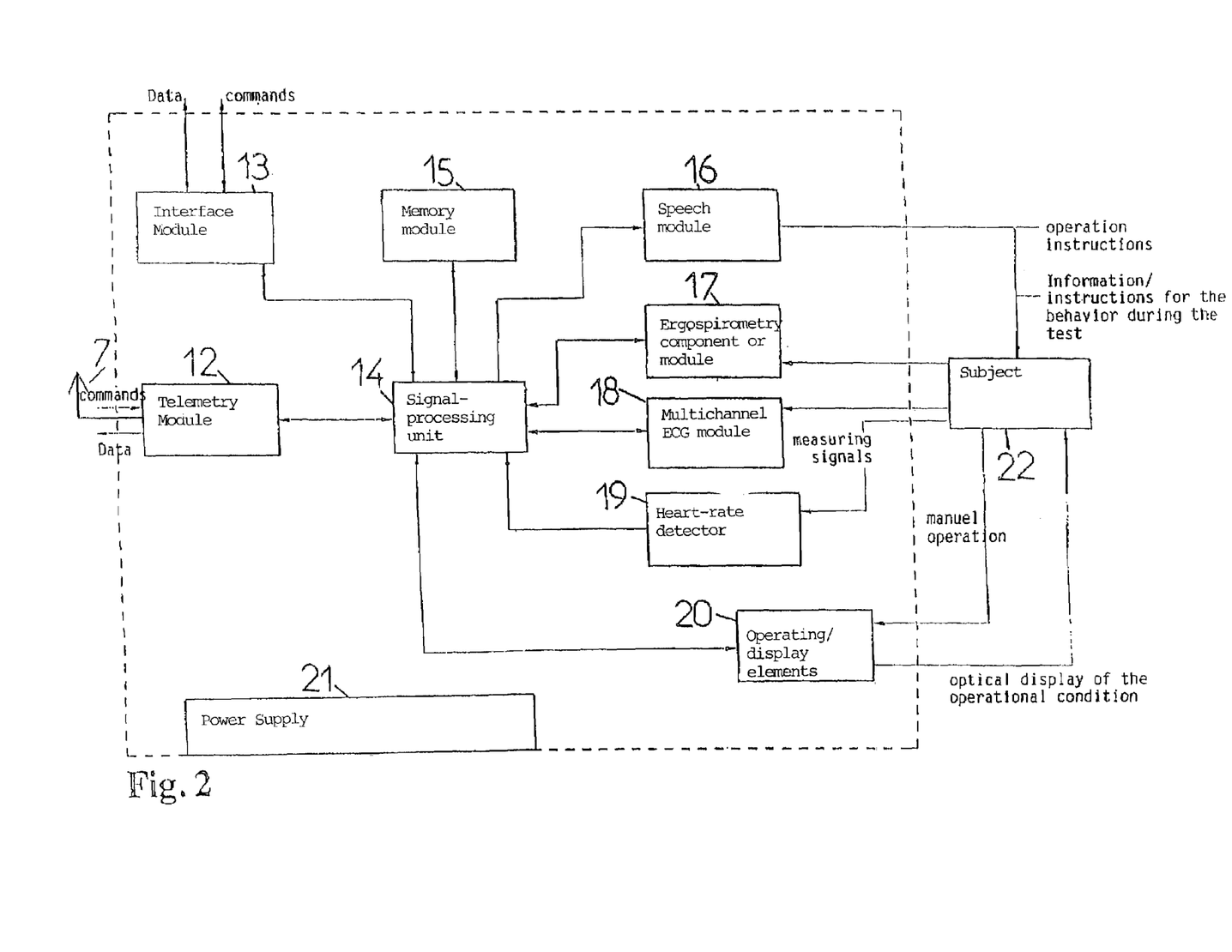
FIG. 2 is a block diagram of the portable measurement unit.

According to the block diagram in FIG. 2, the portable measurement unit includes a telemetry module 12 with transmission and reception antenna 7, which is capable of creating a bidirectional connection with the telemetry unit of the base station.

An interface module 13 mediates direct communication with a device that can be connected thereto, such as a personal computer, a computer-assisted base station or another medical-technical device.

A signal-processing system 14 governs the execution of all monitoring and controlling operations, and also controls the calculation and storage of the data obtained in the portable measurement unit. For the latter purpose a memory module 15 is connected to the signal-processing unit 14, which in addition is connected to a speech module 16 provided for the output of vocal operating instructions and for the acoustic presentation of data. The ergospirometry component 17 is supervised by the signal processor 14 and, according to FIG. 1, receives input from the subject or patient 22. Other measurement signals are sent to a multichannel ECG 18, and in addition the momentary heart rate of the subject is monitored by a heart-rate detector 19.

Operation and display means 20 are provided to initiate measurement sequences and/or signal momentary states of the measurement unit by way of the signal processor, so that the subject is sufficiently well informed and, where appropriate, can manually influence the course of the measurements.

A power-supply module 21 contains both secondary elements and circuitry for electronic voltage stabilization, with the aim of minimizing the overall power consumption of the measurement unit; for example, modules or units that are not needed for the moment, because their function does not contribute to the current measurement process, can be put into a so-called sleep mode.

Figure 3:
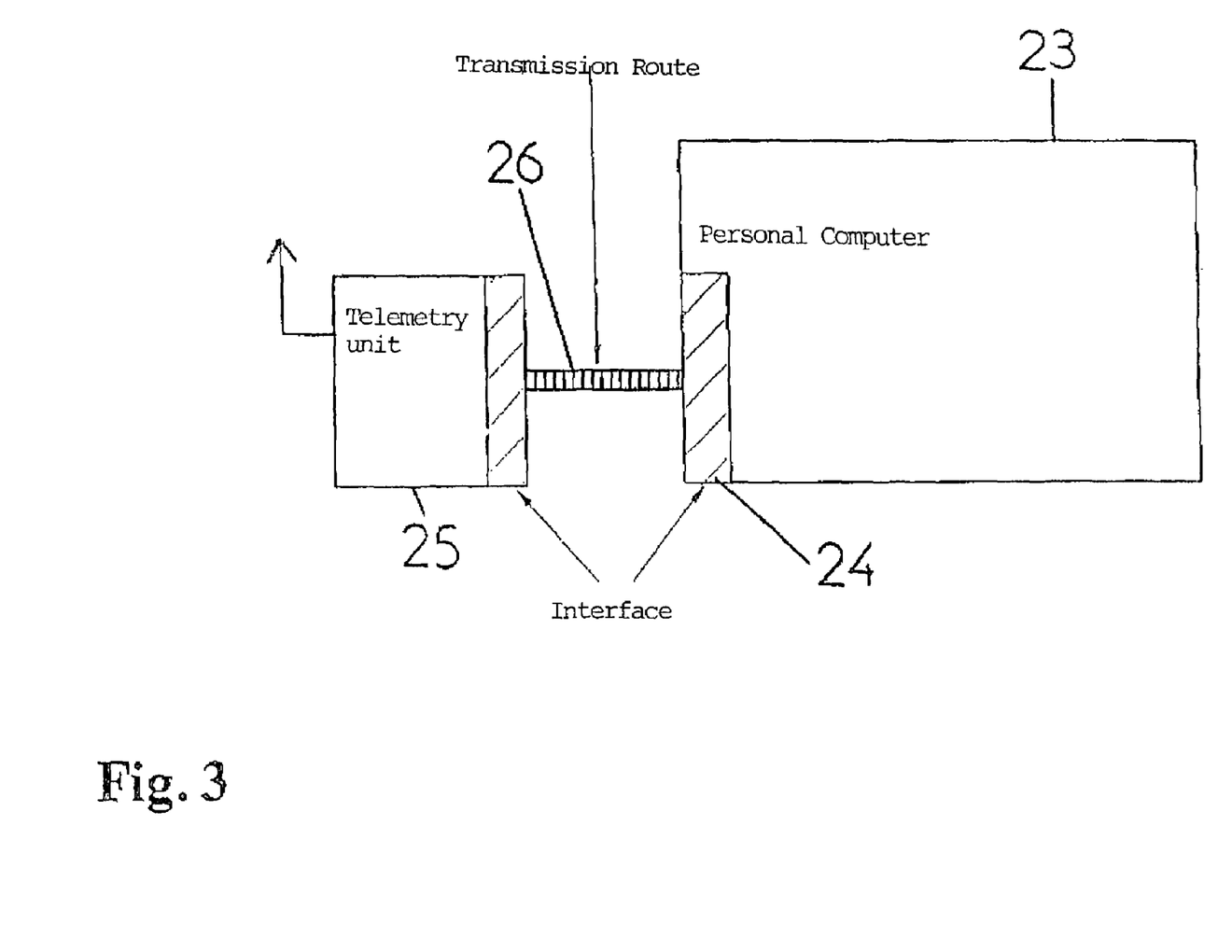
FIG. 3 shows the base station with telemetry module.

The base station according to FIG. 3 consists of a personal computer 23 with an interface 24 by way of which a connection to a telemetry unit 25 can be created. The telemetry unit 25 can be situated at some distance from the personal computer 23 and communicate therewith by a transmission means 26, which may be implemented by a wireless (infrared) or wired connection; preferably, the purpose of this separation is to achieve a relative positioning that is optimal for creation of the actual high-frequency telemetric connection.

By means of processors in the measurement unit or by way of the personal computer 23 and the software provided therein, the frequency for telemetry can be selected automatically. For instance, after scanning of the frequency band and/or following a trial with test data, the particular frequency that is likely to provide optimal transmission quality in the current circumstances can be selected and set.

For example, a frequency range of substantially 430 to 470 MHz can be scanned, although of course other frequency ranges can be provided, depending on country-specific constraints.

Figure 4:
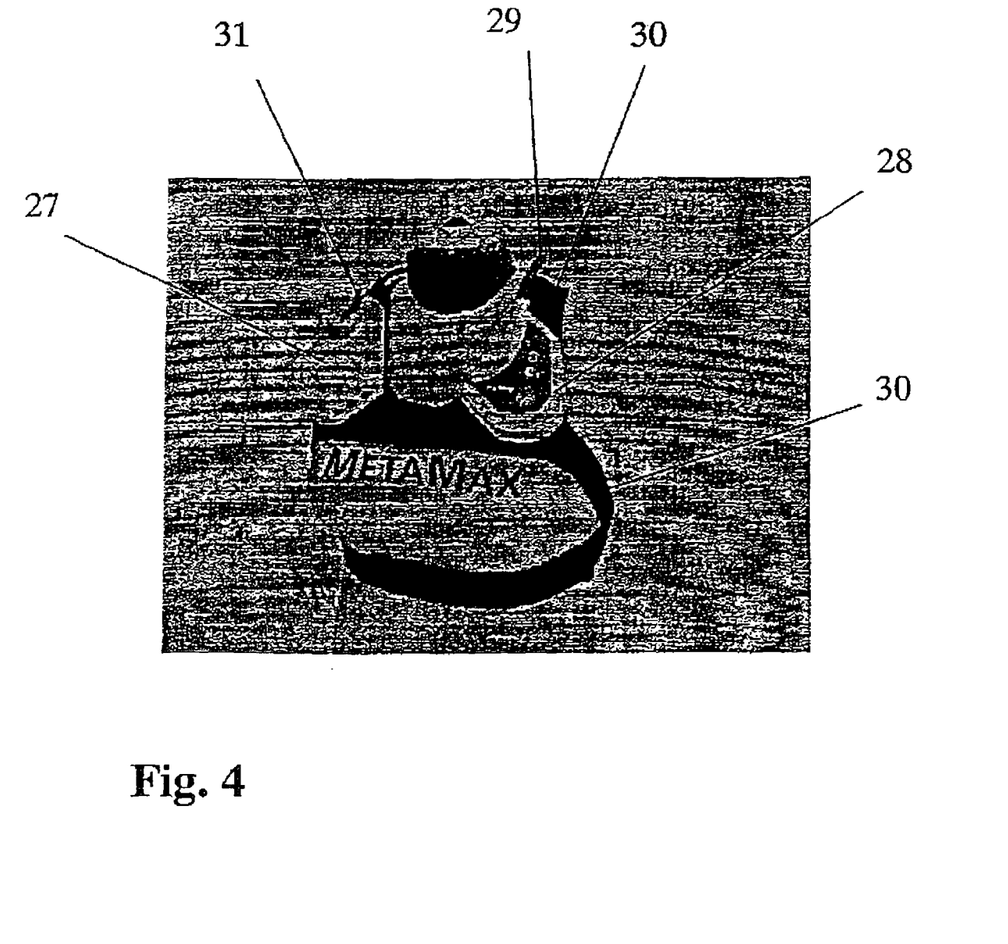
FIG. 4 is a representation of a mobile ergospirometry system to show how its two housing components can be attached to the body of a subject by a carrier system.

In an exemplary embodiment of the portable measurement unit according to FIG. 4, the unit is designed in the form of two housing components 27 and 28, which are-electrically-connected to one another by a cable 29.

A special harness 30 is attached to the subject's body and accommodates the housing components in an upper region of the body, preferably in the vicinity of the shoulders/clavicle.

The housing component 27 contains, among other things, the telemetry module with antenna 31. Operating and display elements not shown individually here, as well as pin-and-socket connectors, assist operation of the measurement unit with respect to the connection of an earphone for vocal communication. Because the housing components 27 and 28 are positioned on the upper body as shown in the picture, the subject is only minimally impeded in carring out the particular activities required for stress tests, and the favorable position of the antenna produces an optimal transmission route for telemetry.

Altogether, then, the invention succeeds in providing a novel, further developed mobile ergospirometry system, by means of which respiratory-gas analyses can be carried out in combination with the measurement of cardiological parameters in largely natural conditions and stress situations; furthermore, the person conducting the test is enabled to use a bidirectional telemetry transmission route not only to collect the measured data online and to evaluate them, but also to influence the course of the test directly by sending out instructions as to behavior or by intervening in the control of the measurement unit.

LIST OF REFERENCE NUMERALS

1 Mask/mouthpiece
2 Flow/volume sensor
3 Suction line
4; 5 $CO_2/O_2$ sensor
6 Data collection unit
7 Transmission/reception antenna of the telemetry module
8 Control unit
9 Pump
10 Temperature sensor
11 Humidity sensor
12 Telemetry module
13 Interface module
14 Signal-processing unit
15 Memory module
16 Speech module
17 Ergospirometry component or module
18 Multichannel ECG module
19 Heart-rate detector
20 Operating/display elements
21 Power supply
22 Subject
23 Personal computer
24 Interface
25 Telemetry unit
26 Transmission route
27; 28 Housing components
29 Connecting cable
30 Harness
31 Antenna

What is claimed is:

1. Mobile ergospirometry system, comprising:
   a portable measurement unit configured to be attached to a subject and incorporating a mouthpiece or mask to collect respiratory gas;
   a sensor configured to sense a volume or amount of gas and at least one respiratory gas sensor configured to determine at least one of a $CO_2$ and an $O_2$ concentration in the respiratory gas;
   a signal processing unit, a telemetry module, and a computer-assisted base station having a telemetry unit configured to create a wireless connection to the telemetry module;
   wherein by the telemetry module a bidirectional transmission route to the telemetry unit is set up to transmit data and commands, for which purpose a transmitter and receiver subassembly is provided, so that the base station may communicate online information or requirements for operation of the measurement unit and/or to modify a course of a test, wherein the signal processing unit sends received coded commands to a speech module for conversion and audio output of information,
   wherein the measurement unit further comprises a heart-rate detector and a multichannel ECG module, such that detection and storage of ergospirometric and cardiological data are performed synchronously by the signal processing unit, and
   further comprising a memory configured to back up data in the measurement unit, such that, in the memory data, sets are stored in a specified format and comprise data specifically related to each consecutive breath and/or complete sequence of data measured for all or selected parameters during selectable intervals with selectable starting times.

2. Mobile ergospirometry system, comprising:

a portable measurement unit configured to be attached to a subject and incorporating a mouthpiece or mask to collect respiratory gas;

a sensor configured to sense a volume or amount of gas and at least one respiratory gas sensor configured to determine at least one of a $CO_2$ and an $O_2$ concentration in the respiratory gas;

a signal processing unit, a telemetry module, and a computer-assisted base station having a telemetry unit configured to create a wireless connection to the telemetry module;

wherein by the telemetry module a bidirectional transmission route to the telemetry unit is set up to transmit data and commands, for which purpose a transmitter and receiver subassembly is provided, so that the base station may communicate online information or requirements for operation of the measurement unit and to modify a course of a test, wherein the signal processing unit sends received coded commands to a speech module for conversion and audio output of information, wherein the speech module comprises a digital memory in which are stored words, word groups, or other mechanisms of presenting information acoustically, and wherein by the signal processing unit, from the words or word groups stored in the digital memory command-oriented word combinations appropriate to a current situation are selected, linked, and output in a controlled manner.

3. Mobile ergospirometry system, comprising:

a portable measurement unit configured to be attached to a subject and incorporating a mouthpiece or mask to collect respiratory gas;

a sensor configured to sense a volume or amount of gas and at least one respiratory gas sensor configured to determine at least one of a $CO_2$ and an $O_2$ concentration in the respiratory gas;

a signal processing unit, a telemetry module, and a computer-assisted base station having a telemetry unit configured to create a wireless connection to the telemetry module;

wherein by the telemetry module a bidirectional transmission route to the telemetry unit is set up to transmit data and commands, for which purpose a transmitter and receiver subassembly is provided, so that the base station may communicate online information or requirements for operation of the measurement unit and to modify a course of a test, wherein the signal processing unit sends received coded commands to a speech module for conversion and audio output of information, wherein the measurement unit comprises at least one sensor configured to detect at least one of a quantity of an ambient temperature, humidity of the respiratory gas, and differential pressure values, these detected quantities being used to calibrate and correct values signalled by the at least one respiratory gas sensor.

4. Mobile ergospirometry system, comprising:

a portable measurement unit configured to be attached to a subject and incorporating a mouthpiece or mask to collect respiratory gas;

a sensor configured to sense a volume or amount of gas and at least one respiratory gas sensor configured to determine at least one of a $CO_2$ and an $O_2$ concentration in the respiratory gas;

a signal processing unit, a telemetry module, and a computer-assisted base station having a telemetry unit configured to create a wireless connection to the telemetry module;

wherein by the telemetry module a bidirectional transmission route to the telemetry unit is set up to transmit data and commands, for which purpose a transmitter and receiver subassembly is provided, so that the base station may communicate online information or requirements for operation of the measurement unit and/or to modify a course of a test, wherein the signal processing unit sends received coded commands to a speech module for conversion and audio output of information, and wherein the portable measurement unit includes two housing components connected by a cable, and wherein by a carrier harness or frame the housing components are each adapted to be positioned on an upper body of the subject in a vicinity of shoulders/clavicle of the subject.

5. Mobile ergospirometry system, comprising:

a portable measurement unit configured to be attached to a subject and incorporating a mouthpiece or mask to collect respiratory gas;

a sensor configured to sense a volume or amount of gas and at least one respiratory gas sensor configured to determine at least one of a $CO_2$ and an $O_2$ concentration in the respiratory gas;

a signal processing unit, a telemetry module, and a computer-assisted base station having a telemetry unit configured to create a wireless connection to the telemetry module;

wherein by the telemetry module a bidirectional transmission route to the telemetry unit is set up to transmit data and commands, for which purpose a transmitter and receiver subassembly is provided, so that the base station may communicate online information or requirements for operation of the measurement unit and to modify a course of a test, wherein the signal processing unit sends received coded commands to a speech module for conversion and audio output of information, wherein the telemetry unit in the base station comprises an automatic frequency-selection device, so that after scanning of a frequency band and/or after a procedure for transmitting test data, a telemetry frequency can be set that is expected to provide optimal transmission quality.

6. Mobile ergospirometry system according to claim 5, wherein the measurement unit further comprises a heart-rate detector and a multichannel ECG module, such that detection and storage of ergospirometric and cardiological data are performed synchronously by the signal processing unit.

7. Mobile ergospirometry system according to claim 6, further comprising a memory configured to back up data in the measurement unit, such that, in the memory data, sets are stored in a specified format and comprise data specifically related to each consecutive breath and/or complete sequence of data measured for all or selected parameters during selectable intervals with selectable starting times.

8. Mobile ergospirometry system according to claim 7, wherein by the signal processing unit ergospirometric parameters are calculated from the data obtained, and these calculated parameters are stored in the memory and/or are configured to be displayed or acoustically communicated.

9. Mobile ergospirometry system according to claim 5, wherein the signal processing unit, with or without an external command, derives from available measured data and/or from progress of the test instructions regarding the subject's behavior and transmits the instructions to the subject by the speech module.

10. Mobile ergospirometry system according to claim 5, wherein the speech module comprises a digital memory in which are stored words, word groups, or other mechanisms of presenting information acoustically.

11. Mobile ergospirometry system according to claim 10, wherein by the signal processing unit, from the words or word groups stored in the digital memory command-oriented word combinations appropriate to a current situation are selected, linked, and output in a controlled manner.

12. Mobile ergospirometry system according to claim 5, wherein the measurement unit comprises at least one sensor configured to detect at least one of a quantity of an ambient temperature, humidity of the respiratory gas, and differential pressure values, these detected quantities being used to calibrate and correct values signalled by the at least one respiratory gas sensor.

13. Mobile ergospirometry system according to claim 5, wherein the portable measurement unit comprises an interface for exchanging data with the base station, a personal computer, or a medical-technical device.

14. Mobile ergospirometry system according to claim 5, wherein the base station comprises an interface to create a connection with a bidirectional telemetry unit designed as a supplementary subassembly.

15. Mobile ergospirometry system according to claim 5, wherein the portable measurement unit includes two housing components connected by a cable, and wherein by a carrier harness or frame the housing components are each adapted to be positioned on an upper body of the subject in a vicinity of shoulders/clavicle of the subject.

* * * * *